(12) United States Patent
Dietz et al.

(10) Patent No.: US 8,148,286 B2
(45) Date of Patent: Apr. 3, 2012

(54) ACTIVATED ALKALINE EARTH METAL, IN PARTICULAR MAGNESIUM, FOR THE PREPARATION OF ORGANOALKALINE EARTH METAL COMPOUNDS

(75) Inventors: Rainer Dietz, Egelsbach (DE); Ute Emmel, Frankfurt am Main (DE); Ulrich Wietelmann, Friedrichsdorf (DE); Uwe Lischka, Frankfurt am Main (DE)

(73) Assignee: Chemetall GmbH, Frankfurt am Main (DE)

( * ) Notice: Subject to any disclaimer, the term of this patent is extended or adjusted under 35 U.S.C. 154(b) by 994 days.

(21) Appl. No.: 11/991,122

(22) PCT Filed: Sep. 1, 2006

(86) PCT No.: PCT/EP2006/065917
§ 371 (c)(1),
(2), (4) Date: Feb. 27, 2008

(87) PCT Pub. No.: WO2007/026016
PCT Pub. Date: Mar. 8, 2007

(65) Prior Publication Data
US 2009/0112027 A1 Apr. 30, 2009

(30) Foreign Application Priority Data
Sep. 1, 2005 (DE) .......................... 10 2005 041 784

(51) Int. Cl.
*B01J 21/10* (2006.01)
(52) U.S. Cl. ......... 502/115; 502/102; 502/103; 502/104
(58) Field of Classification Search .................. 502/102, 502/103, 104, 115
See application file for complete search history.

(56) References Cited

U.S. PATENT DOCUMENTS

| | | |
|---|---|---|
| 3,758,620 A | 9/1973 | Vit |
| 5,093,443 A | 3/1992 | Nowlin |
| 6,297,188 B1 | 10/2001 | Schork et al. |

FOREIGN PATENT DOCUMENTS

| | | |
|---|---|---|
| EP | 0 997 451 | 5/2000 |
| SU | 477 626 A | 8/1985 |
| WO | WO 91/05608 A | 5/1991 |

OTHER PUBLICATIONS

Tilstam, et al. "Activation of Mg Metal for Safe Formation of Grignard Reagents on Plant Scale", *Org. Proc. Research & Dev.* (2002) 6, pp. 906-910.

*Primary Examiner* — Elvis O Price
(74) *Attorney, Agent, or Firm* — Fulbright & Jaworski L.L.P.

(57) ABSTRACT

The invention relates to an activated alkaline earth metal, to a method for its production and the use of the activated alkaline earth metal for the preparation of Grignard compounds and organoalkaline earth metal compounds.

55 Claims, No Drawings

ACTIVATED ALKALINE EARTH METAL, IN PARTICULAR MAGNESIUM, FOR THE PREPARATION OF ORGANOALKALINE EARTH METAL COMPOUNDS

This application is a §371 of PCT/EP2006/065917 filed Sep. 1, 2006, which claims priority from German Patent Application No. DE 10 2005 041 784.1 filed Sep. 1, 2005.

The present invention provides an activated alkaline-earth metal, a process for the preparation thereof and the use of the activated alkaline-earth metal.

Alkaline-earth metal, in particular magnesium, is available for supply in a wide variety of forms, such as e.g. powders, chips, granules, bars etc., including on an industrial scale. In chemistry, magnesium is used e.g. as a raw material for the preparation of dialkylmagnesium compounds, alkylmagnesium halides, in particular Grignard compounds, magnesium alkoxides, magnesium bis(dialkyl)amides and magnesium hydride.

Diagram 1: Preparation of magnesium compounds from metallic magnesium:

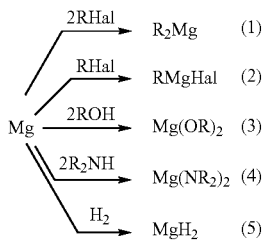

Hal = Cl, Br, I
R = alkyl or aryl

The reactions according to (1) to (4) are normally carried out in an aprotic solvent or solvent mixture. When the aforementioned reactions are carried out in practice, it is generally observed that the desired reaction is inhibited, i.e. no reaction takes place. This is because commercially available metallic magnesium is coated with a compact layer of corrosion products, which is impenetrable to the reagents listed in diagram 1 above. To remove this layer, in the case of Grignard synthesis (reaction (2)) in coordinating solvents, e.g. tetrahydrofuran (THF), various activation methods have been developed (review: U. Tilstam and H. Weinmann, Org. Proc. Dev. 2002, 6, 909-910):

1. Dissolving the oxide layer in mineral acids.
   Disadvantage: this process requires a subsequent washing step under inert gas, in which all traces of acid are removed. On an industrial scale, this can be accomplished only with great difficulty.
2. Dry stirring or grinding: this results in partial mechanical removal of the protective layer.
   Disadvantage: this process is also very difficult to implement on a larger scale, since the material of the vessel, often consisting of glass or vitreous enamel, is damaged as a result, and stirring elements generally do not reach deep enough into a stirred vessel.
3. Addition of finished Grignard reagent: this method is a tried and tested means for several consecutive batches.
   Disadvantage: at the beginning of a campaign, however, there is generally no finished product available.
4. Activation by iodine or dibromoethane.
   Disadvantage: iodine is strongly corrosive and dibromoethane is a carcinogen. Both agents are therefore of low suitability for industrial synthesis.
5. Aluminium hydride activation: the addition of sodium bis(2-methoxyethoxy)aluminium hydride or diisobutylaluminium hydride (DiBAH) is said to activate magnesium in ethereal solvents, such as diethyl ether or THF, for subsequent reaction with organic halides.
   Disadvantage: in diethyl ether, 5 to 12 mole % of aluminium compound (based on magnesium metal used) is needed for this purpose (U.S. Pat. No. 3,758,620); in THF, 1 mole % is required.

Many of the compounds listed in diagram 1, in particular the dialkylmagnesium compounds (1) and magnesium alcoholates (3), are required primarily for applications in olefin or diene polymerisation. For this use, the magnesium compounds employed must contain no donor solvents whatsoever, in particular no ethers. Instead, either dry, solvent-free products or preferably solutions in non-coordinating solvent systems, particularly in aromatic or aliphatic hydrocarbons, are used for such a purpose. Furthermore, the compounds used for polymerisation initiation, e.g. Ziegler-Natta catalysts, should not contain any impurities that have a disadvantageous effect on the application properties. An example of an impurity that is disadvantageous in this way is iodine (EP-A-997 451).

The object of the invention is therefore to provide an activated alkaline-earth metal which overcomes the disadvantages of the prior art.

According to the invention, the object is surprisingly achieved by the features of the main claim. Preferably embodiments are found in the subclaims.

It is a further object of the invention to provide a process for the preparation of the activated alkaline-earth metal.

Activated alkaline-earth metal within the meaning of the invention means that the alkaline-earth metal reacts with organic halides and/or alcohols instantaneously, i.e. at least as rapidly as after activation by the methods described in points 1 to 5.

In this case, the activation of the alkaline-earth metal takes place in particular in non-coordinating solvents. The activated alkaline-earth metal should not contain any unwanted impurities, e.g. iodine.

According to the invention, metallic alkaline-earth metal, preferably metallic magnesium, either in pure, solvent-free form or in the presence of one or more non-coordinating solvents, is brought into contact in this process with aluminium compounds of the general formula $AlR_{3-n}Hal_n$, hereinafter referred to as activating agents. As a result, the metallic alkaline-earth metal is activated, i.e. its reactivity is increased.

Both here and below, the following are to be understood:
the residue R as an alkyl or aryl residue, preferably as an alkyl residue, particularly preferably as an alkyl residue with 1 to 8 C atoms;
the residue Hal as a halogen residue, preferably as a chlorine, bromine or iodine residue;
n as a number, with $0 \leq n \leq 2$.

Surprisingly, it has been found that the activating agents according to the invention, even in very low concentrations, e.g. in concentrations of 0.001 to 2 mole %, preferably in concentrations of 0.1 to 1.5 mole %, based on alkaline-earth metal used, are able to increase the reactivity of the alkaline-earth metal in such a way that the desired products, in particular dialkylmagnesium compounds and magnesium alcoholates, can be synthesised without an induction period and in high yields. In principle, however, larger quantities of activating agent, e.g. 10 or even over 20 mole %, can also be used. The increased addition of activating agent has the advantage that the viscosity of the alkoxide solutions is reduced. This makes these solutions easier to transport.

The activating agent is preferably added to the suspension of the alkaline-earth metal in the non-coordinating solvent.

The process according to the invention for the preparation of the activated alkaline-earth metal is generally carried out as described below, without limiting the invention thereto:

Alkaline-earth metal is presented in a non-coordinating solvent, preferably in aromatic or aliphatic hydrocarbons, particularly preferably in toluene, n-hexane, n-octane or mixtures of at least two of these, and the activating agent is added while stirring. It is important that air and moisture are excluded while these operations are undertaken, preferably working under inert gas, particularly preferably under argon, helium or nitrogen. In this way, the partial or complete decomposition of the activating agents, which are generally sensitive to air, is avoided. Under inert conditions, therefore, significantly smaller quantities of activating agent are required than is the case in the presence of oxygen, water or other reactive substances.

The metal activation process takes place at temperatures of 0 to 150° C., preferably 20 to 110° C. The contact period is from one minute to 5 hours, preferably from 5 minutes to one hour. The contact period is dependent here on the concentration of the activating agent and the nature, i.e. the thickness and compactness, of the layer passivating the metal.

The activated alkaline-earth metal according to the invention is obtained.

Commercially available magnesium, preferably in the form of turnings, granules or powder, is preferably used as the alkaline-earth metal.

The compounds of the formula $AlR_{3-n}Hal_n$ already described are used as activating agents. The activating agent is preferably selected from trimethylaluminium (TMA), triethylaluminium (TEA), tributylaluminium (TBA), ethylaluminium dichloride (EADC) and/or diethylaluminium chloride (DEAC) or mixtures of two or more of these compounds. These compounds are available in commercial quantities as pure substances or as solutions in hydrocarbons.

The activated alkaline-earth metal according to the invention can be used as follows, for example, without limiting the invention thereto:

On completion of activation, the metering of the alcohol or of the mixture of two or more alcohols or of the alkyl halide or of the mixture of two or more alkyl halides can be commenced. The metering takes place over a period of a few minutes to several hours, depending on the batch size and other attendant circumstances relating to the apparatus. A period of one to two hours is typically meaningful. The reaction takes place in the temperature range between room temperature (RT) and about 150° C. If it is carried out under normal pressure, the upper temperature limit is set by the boiling point of the solvent, i.e. for example 110° C. for toluene or about 65° C. for n-hexane.

The reaction is preferably carried out at the boiling point if the thermal stability of the product formed permits this.

The product work-up takes place as a function of the physico-chemical properties of the end product. Insoluble products, such as e.g. magnesium ethoxide, are obtained in pure, i.e. solvent-free, form by solid-liquid separation or total evaporation. If a metal-free product is desired, complete conversion must be ensured. The alcohol employed ethanol in the case of the synthesis of magnesium ethoxide—or the organic halide is used in at least the stoichiometric quantity but preferably with a 0.1 to 60% excess.

If a compound soluble in the non-coordinating solvent or solvent mixture, e.g. magnesium ethyl hexoxide, is being produced, the reaction product can be separated off from unaltered magnesium metal by simple means, e.g. by filtration. In such a case, the metal may be used in excess. This is sensible particularly when the product solution should contain the smallest possible amounts of free alcohol or organic halide.

The present invention provides in detail:

an activated alkaline-earth metal which reacts instantaneously with organic halides and/or alcohols;

an activated alkaline-earth metal which is obtainable by adding an activating compound in a solvent to the alkaline-earth metal, the activating compound corresponding to the general formula $AlR_{3-n}Hal_n$ and the solvent being selected from non-coordinating solvents.

an activated alkaline-earth metal which is obtainable by adding an activating compound of the general formula $AlR_{3-n}Hal_n$ in a non-coordinating solvent to the alkaline-earth metal, the compounds of the general formula $AlR_{3-n}Hal_n$ being selected from trimethylaluminium (TMA), triethylaluminium (TEA), tributylaluminium (TBA), ethylaluminium dichloride (EADC) and/or diethylaluminium chloride (DEAC) or mixtures of two or more of these compounds;

an activated alkaline-earth metal which is obtainable by adding an activating compound of the general formula $AlR_{3-n}Hal_n$ in a non-coordinating solvent to the alkaline-earth metal, the non-coordinating solvents being selected from aromatic or aliphatic hydrocarbons or from mixtures of these solvents;

an activated alkaline-earth metal which is obtainable by adding an activating compound of the general formula $AlR_{3-n}Hal_n$ in a non-coordinating solvent to the alkaline-earth metal, the non-coordinating solvents being selected from toluene, n-hexane, n-octane or mixtures of at least two of these solvents;

an activated alkaline-earth metal which is obtainable by adding an activating compound of the general formula $AlR_{3-n}Hal_n$ in a non-coordinating solvent to the alkaline-earth metal, the alkaline-earth metal being beryllium, magnesium, calcium, strontium or barium, preferably magnesium, calcium or barium, particularly preferably magnesium;

a mixture which contains an activated alkaline-earth metal according to the invention in a solvent, preferably a non-coordinating solvent;

a mixture which contains an activated alkaline-earth metal according to the invention in a solvent, preferably a non-coordinating solvent, and an activating compound of the general formula $AlR_{3-n}Hal_n$;

a process for the preparation of activated alkaline-earth metal by reacting alkaline-earth metal with compounds of the general formula $AlR_{3-n}Hal_n$ in non-coordinating solvents;

a process for the preparation of activated alkaline-earth metal by reacting alkaline-earth metal with compounds of the general formula $AlR_{3-n}Hal_n$ in non-coordinating solvents, comprising the following process steps:

presenting the alkaline-earth metal in a non-coordinating solvent under inert conditions;

adding one or more compounds of the general formula $AlR_{3-n}Hal_n$ while stirring;

a process for the preparation of activated alkaline-earth metal, wherein the compounds of the general formula $AlR_{3-n}Hal_n$ are selected from trimethylaluminium (TMA), triethylaluminium (TEA), tributylaluminium (TBA), ethylaluminium dichloride (EADC) and/or diethylaluminium chloride (DEAC) or mixtures of two or more of these compounds;

a process for the preparation of activated alkaline-earth metal, wherein the non-coordinating solvents are selected from aromatic or aliphatic hydrocarbons or mixtures of these solvents;

a process for the preparation of activated alkaline-earth metal, wherein the non-coordinating solvents are selected from toluene, n-hexane, n-octane or mixtures of at least two of these solvents;

a process for the preparation of activated alkaline-earth metal, wherein the alkaline-earth metal is beryllium, magnesium, calcium, strontium or barium, preferably magnesium, calcium or barium, particularly preferably magnesium;

a process for the preparation of activated alkaline-earth metal, wherein the compounds of the general formula $AlR_{3-n}Hal_n$ are added to the alkaline-earth metal in concentrations of 0.001 to 2 mole %, preferably in concentrations of 0.1 to 1.5 mole %, based on alkaline-earth metal used;

a process for the preparation of activated alkaline-earth metal, wherein the compounds of the general formula $AlR_{3-n}Hal_n$ are added to the alkaline-earth metal in concentrations of up to 10 mole %, preferably in concentrations of up to 20 mole % and more;

a process for the preparation of activated alkaline-earth metal, wherein the metal activation process takes place at temperatures of between 0 and 150° C., preferably between 20 and 110° C.;

a process for the preparation of activated alkaline-earth metal, wherein the contact period is between one minute and 5 hours, preferably between 5 minutes and one hour;

the use of activated alkaline-earth metal for the preparation of alkaline-earth metal alkoxides;

the use of activated alkaline-earth metal for the preparation of magnesium, calcium and barium alkoxides;

the use of activated magnesium metal for the preparation of dialkylmagnesium compounds, alkyl-magnesium halides, in particular Grignard compounds, magnesium alkoxides, magnesium bis(dialkyl)amides and magnesium hydride.

The invention is explained below by examples, without being limited thereto:

EXAMPLE 1

Preparation of a Granular Magnesium Ethoxide by Reacting Fine Magnesium Turnings with Ethanol in a Toluene Suspension 77.3 g (3180 mmol) of fine magnesium turnings (NF2 from Minmet) in 1400 g of toluene are charged into an inerted 3-liter reactor having a double-walled jacket and provided with a propeller agitator, dropping funnel and reflux condenser. This is then heated to 50° C. with stirring, and 10 ml of a 25% triethylaluminium solution in toluene are added. At the specified temperature, stirring is carried out for 30 minutes and then the metered addition of anhydrous ethanol is commenced. A total of 307 g of ethanol (6660 mmol, 4.7% excess) was added over a period of 1.5 hours. The reaction starts almost instantaneously, which can be detected from the temperature increase and gas formation. The internal temperature is limited to 65° C. by counter-cooling. On completion of the addition, 55 l of gas have formed ($\hat{=}$72% of theory).

The jacket temperature is then increased to 90° C. After a post-reaction time of 100 minutes, the gas formation comes to a standstill. A total of 75.8 l of gas ($\hat{=}$99% of theory) has formed.

The reaction mixture is emptied on to a fritted glass filter and the toluene phase is separated off. The filter residue is washed with hexane and initially pre-dried at room temperature. For the final drying, the solid is placed in a 1-liter round-bottom flask and dried at 110° C. in vacuo.

338 g (93% of theory) of a granulated material with a dust content of 1.5% are obtained.

The reaction conditions and results are recorded in table 1 and table 2.

EXAMPLE 2

Preparation of a Granular Magnesium Ethoxide by Reacting Granular Magnesium with Ethanol in a Toluene Suspension In the same apparatus as in example 1, granular magnesium is activated with triethylaluminium in toluene and reacted with ethanol. The reaction conditions and results are recorded in table 1 and table 2.

EXAMPLE 3

Preparation of a Granular Magnesium Ethoxide by Reacting Coarse Magnesium Turnings with Ethanol in a Toluene Suspension In the same apparatus as in example 1, coarse magnesium turnings are activated with triethylaluminium in toluene and reacted with ethanol. The reaction conditions and results are recorded in table 1 and table 2.

EXAMPLE 4

Preparation of Magnesium Ethyl Hexoxide in Toluene 11.2 g of magnesium turnings in 220 ml of toluene are charged into a 1-liter reactor having a double-walled jacket. After heating to 50° C., 5 ml of a 25% triethylaluminium solution in toluene are added and the mixture is stirred for 30 minutes. It is then heated to 110° C. and 55.5 g of 2-ethylhexanol are added dropwise within 2 hours. The reaction starts immediately. After a total of 3 hours, 4.9 l of gas have formed.

After cooling to 80° C., the mixture is filtered through a G3 filter. The yield is 269 g of a 19% viscous solution of magnesium ethyl hexoxide in toluene.

EXAMPLE 5

Preparation of Barium Ethyl Hexoxide in n-Octane 66 mmol of barium chips in 150 ml of octane are charged into a 250 ml glass flask and 0.5 ml of a 25% triethylaluminium solution in toluene are added. The mixture is heated to 130° C. and 122 mmol ethylhexanol are added.

After a reaction period of 5 hours at 130° C., 1.6 l of gas have formed.

After filtration, 162 g of a 13.5% solution of barium ethyl hexoxide in n-octane are obtained.

EXAMPLE 6

Preparation of Calcium Ethyl Hexoxide in n-octane 65 mmol of calcium chips in 120 g of octane are charged into the same apparatus as example 5 and activated with 1.5 mole % triethylaluminium solution, and 140 mmol of ethylhexanol are added at 120 to 130° C. After a reaction period of 6 hours, no further gas is formed.

145 g of a 4% solution of calcium ethyl hexoxide in n-octane are obtained.

COMPARATIVE EXAMPLE 1

Preparation of Magnesium Ethoxide by Reaction of Magnesium in Anhydrous Ethanol In the apparatus from example 1, 76 g of fine magnesium turnings are suspended in 2.05 kg of anhydrous ethanol (water content according to Karl Fischer: 36 ppm) and the jacket temperature is increased to 90° C. within 20 minutes so that the contents of the reactor boil. After a total of 70 minutes, a scant 20 l of gas (approx. 26% of theory) have formed. The rate of gas formation then decreases markedly. Within a further 4 hours of reflux boiling, only 21 l of gas are released. 0.8 g of iodine are then added and, after a further hour, 1.8 g of iron chloride. The rate of gas formation then increased just briefly. After refluxing for a total of 15 and 20 hours respectively, 57.6 and 65.5 l of gas respectively have formed (approx. 77 and 87% of theory respectively).

The greyish-white suspension is filtered and vacuum dried at 110° C. The finished product consists predominantly of a fine powder with a very high dust content. In addition to lumps, it still contains about 10% of unreacted metallic magnesium.

The most important reaction conditions and results are recorded in table 1 and table 2.

TABLE 1

Preparation of granular magnesium ethoxide

| Example | Magnesium | | Toluene (g) | Ethanol | | TEA* | |
|---|---|---|---|---|---|---|---|
| | Type | Amount (g) | | (g) | (% of theory) | (g) | (mol %) |
| 1 | Fine turnings | 77.3 | 1400 | 307 | 105 | 2.5 | 0.7 |
| 2 | Granules | 80.5 | 1550 | 355 | 116 | 1.1 | 0.3 |
| 3 | Coarse turnings | 65.3 | 1630 | 267 | 108 | 2.3* | 1.2* |
| Cp. 1 | Fine turnings | 76.0 | 0 | 2050 | 712 | — | — |

*Trimethylaluminium

TABLE 2

Preparation results

| Example | Reaction time (h) | Reaction temp. (° C.) | Amount of gas (l) | Amount of product (g) | Appearance | Dust content (%) |
|---|---|---|---|---|---|---|
| 1 | 3.2 | 50-90 | 75.8 | 338 | Granules | 1.5 |
| 2 | 8 | 60-105 | 80.1 | 356 | Granules | <1 |
| 3 | 4 | 90-108 | 64.3 | 281 | Granules | 3 |
| Cp. 1 | 20 | 50-78 | 65.5 | 305 | Powder with lumps | 72 |

In the process according to the invention, magnesium turnings require about 3 to 4 hours for complete conversion to magnesium ethoxide. If more compact, granulated magnesium metal is employed, the reaction times are longer, as can be seen from example 2. The dust content, i.e. the proportion of the end product having a particle size of <0.2 mm, is less than 1%.

The invention claimed is:

1. A process for preparing an activated alkaline-earth metal comprising the step of reacting an alkaline-earth metal with a compound of the formula $AlR_{3-n}Hal_n$ in a non-coordinating solvent to yield the activated alkaline-earth metal;
   wherein R is an alkyl or aryl moiety;
   wherein Hal is halogen; and
   wherein $0 \leq n \leq 2$.

2. The process according to claim 1, wherein the alkaline-earth metal is added to the non-coordinating solvent under inert conditions; and then adding the compound of the formula $AlR_{3-n}Hal_n$ while stirring.

3. The process according to claim 1, wherein the compound of formula $AlR_{3-n}Hal_n$ is at least one of trimethylaluminum, triethylaluminum, tributylaluminum, ethylaluminum dichloride or diethylaluminum chloride.

4. The process according to claim 2, wherein the compound of formula $AlR_{3-n}Hal_n$ is at least one of trimethylaluminum, triethylaluminum, tributylaluminum, ethylaluminum dichloride or diethylaluminum chloride.

5. The process according to claim 1, wherein the non-coordinating solvent comprises at least one of an aromatic hydrocarbon or an aliphatic hydrocarbon.

6. The process according to claim 2, wherein the non-coordinating solvent comprises at least one of an aromatic hydrocarbon or an aliphatic hydrocarbon.

7. The process according to claim 3, wherein the non-coordinating solvent comprises at least one of an aromatic hydrocarbon or an aliphatic hydrocarbon.

8. The process according to claim 4, wherein the non-coordinating solvent comprises at least one of an aromatic hydrocarbon or an aliphatic hydrocarbon.

9. The process according to claim 1, wherein the non-coordinating solvent comprises at least one of toluene, n-hexane or n-octane.

10. The process according to claim 2, wherein the non-coordinating solvent comprises at least one of toluene, n-hexane or n-octane.

11. The process according to claim 3, wherein the non-coordinating solvent comprises at least one of toluene, n-hexane or n-octane.

12. The process according to claim 4, wherein the non-coordinating solvent comprises at least one of toluene, n-hexane or n-octane.

13. The process according to claim 5, wherein the non-coordinating solvent comprises at least one of toluene, n-hexane or n-octane.

14. The process according to claim 1, wherein the alkaline-earth metal is beryllium, magnesium, calcium, strontium or barium.

15. The process according to claim 2, wherein the alkaline-earth metal is beryllium, magnesium, calcium, strontium or barium.

16. The process according to claim 3, wherein the alkaline-earth metal is beryllium, magnesium, calcium, strontium or barium.

17. The process according to claim 4, wherein the alkaline-earth metal is beryllium, magnesium, calcium, strontium or barium.

18. The process according to claim 5, wherein the alkaline-earth metal is beryllium, magnesium, calcium, strontium or barium.

19. The process according to claim 9, wherein the alkaline-earth metal is beryllium, magnesium, calcium, strontium or barium.

20. The process according to claim 1, wherein the compound of formula $AlR_{3-n}Hal_n$ is added to the alkaline-earth metal in a concentration of from 0.001 to 2 mole % based on alkaline-earth metal.

21. The process according to claim 2, wherein the compound of formula $AlR_{3-n}Hal_n$ is added to the alkaline-earth metal in a concentration of from 0.001 to 2 mole % based on alkaline-earth metal.

22. The process according to claim 3, wherein the compound of formula $AlR_{3-n}Hal_n$ is added to the alkaline-earth metal in a concentration of from 0.001 to 2 mole % based on alkaline-earth metal.

23. The process according to claim 4, wherein the compound of formula $AlR_{3-n}Hal_n$ is added to the alkaline-earth metal in a concentration of from 0.001 to 2 mole % based on alkaline-earth metal.

24. The process according to claim 5, wherein the compound of formula $AlR_{3-n}Hal_n$ is added to the alkaline-earth metal in a concentration of from 0.001 to 2 mole % based on alkaline-earth metal.

25. The process according to claim 9, wherein the compound of formula $AlR_{3-n}Hal_n$ is added to the alkaline-earth metal in a concentration of from 0.001 to 2 mole % based on alkaline-earth metal.

26. The process according to claim 14, wherein the compound of formula $AlR_{3-n}Hal_n$ is added to the alkaline-earth metal in a concentration of from 0.001 to 2 mole % based on alkaline-earth metal.

27. The process according to claim 1, wherein the compound of formula $AlR_{3-n}Hal_n$ is added to the alkaline-earth metal in a concentration of at least 10 mole %.

28. The process according to claim 2, wherein the compound of formula $AlR_{3-n}Hal_n$ is added to the alkaline-earth metal in a concentration of at least 10 mole %.

29. The process according to claim 3, wherein the compound of formula $AlR_{3-n}Hal_n$ is added to the alkaline-earth metal in a concentration of at least 10 mole %.

30. The process according to claim 4, wherein the compound of formula $AlR_{3-n}Hal_n$ is added to the alkaline-earth metal in a concentration of at least 10 mole %.

31. The process according to claim 5, wherein the compound of formula $AlR_{3-n}Hal_n$ is added to the alkaline-earth metal in a concentration of at least 10 mole %.

32. The process according to claim 9, wherein the compound of formula $AlR_{3-n}Hal_n$ is added to the alkaline-earth metal in a concentration of at least 10 mole %.

33. The process according to claim 14, wherein the compound of formula $AlR_{3-n}Hal_n$ is added to the alkaline-earth metal in a concentration of at least 10 mole %.

34. The process according to claim 20, wherein the compound of formula $AlR_{3-n}Hal_n$ is added to the alkaline-earth metal in a concentration of at least 10 mole %.

35. The process according to claim 1, wherein the metal is activated during the process at a temperature between 0 and 150° C.

36. The process according to claim 2, wherein the metal is activated during the process at a temperature between 0 and 150° C.

37. The process according to claim 3, wherein the metal is activated during the process at a temperature between 0 and 150° C.

38. The process according to claim 4, wherein the metal is activated during the process at a temperature between 0 and 150° C.

39. The process according to claim 5, wherein the metal is activated during the process at a temperature between 0 and 150° C.

40. The process according to claim 9, wherein the metal is activated during the process at a temperature between 0 and 150° C.

41. The process according to claim 14, wherein the metal is activated during the process at a temperature between 0 and 150° C.

42. The process according to claim 20, wherein the metal is activated during the process at a temperature between 0 and 150° C.

43. The process according to claim 27, wherein the metal is activated during the process at a temperature between 0 and 150° C.

44. The process according to claim 1, wherein a contact period is between one minute and 5 hours.

45. The process according to claim 2, wherein a contact period is between one minute and 5 hours.

46. The process according to claim 3, wherein a contact period is between one minute and 5 hours.

47. The process according to claim 4, wherein a contact period is between one minute and 5 hours.

48. The process according to claim 5, wherein a contact period is between one minute and 5 hours.

49. The process according to claim 9, wherein a contact period is between one minute and 5 hours.

50. The process according to claim 14, wherein a contact period is between one minute and 5 hours.

51. The process according to claim 20, wherein a contact period is between one minute and 5 hours.

52. The process according to claim 27, wherein a contact period is between one minute and 5 hours.

53. The process according to claim 35, wherein a contact period is between one minute and 5 hours.

54. A process according to claim 1, wherein a magnesium, calcium or barium alkoxide is prepared.

55. A process according to claim 1, wherein a dialkylmagnesium compound, an alkylmagnesium halide, a magnesium alkoxide, a magnesium bis(dialkyl)amide or a magnesium hydride are prepared.

* * * * *